United States Patent [19]

Rosenberg

[11] 4,280,507
[45] Jul. 28, 1981

[54] PATIENT CABLE WITH DISTRIBUTED RESISTANCE PROTECTION IN CONDUCTORS

[75] Inventor: Neil A. Rosenberg, Littleton, Mass.

[73] Assignee: Hewlett-Packard Company, Palo Alto, Calif.

[21] Appl. No.: 52,364

[22] Filed: Jun. 27, 1979

[51] Int. Cl.³ .............................................. A61B 5/04
[52] U.S. Cl. ................................................... 128/696
[58] Field of Search ............................... 128/639–644, 128/695, 696, 908, 419 P, 783–786, 798

[56] References Cited

U.S. PATENT DOCUMENTS

| 3,323,514 | 6/1967 | Barrett, Jr. | 128/696 |
| 3,631,851 | 1/1972 | Hesen | 128/696 |
| 3,659,588 | 5/1972 | Kahn et al. | 128/908 |
| 3,812,845 | 5/1974 | Partridge | 128/696 |
| 4,033,355 | 7/1977 | Amundson | 128/419 P |
| 4,109,648 | 8/1978 | Larke et al. | 128/639 |

FOREIGN PATENT DOCUMENTS 1219017  1/1971  United Kingdom ..................... 128/784

Primary Examiner—William E. Kamm
Attorney, Agent, or Firm—Donald N. Timbie

[57] ABSTRACT

A harness for connecting the inputs of an EKG machine or the like to electrodes attached to the body of a patient in which the series resistance required to protect the machine from the presence of high energy pulses applied to the body by a defibrillator is provided by the distributed resistance of shielded conductive carbon loaded polymer leads. Both shields and leads are respectively connected to connectors of a yoke to which EKG leads may be attached.

1 Claim, 8 Drawing Figures

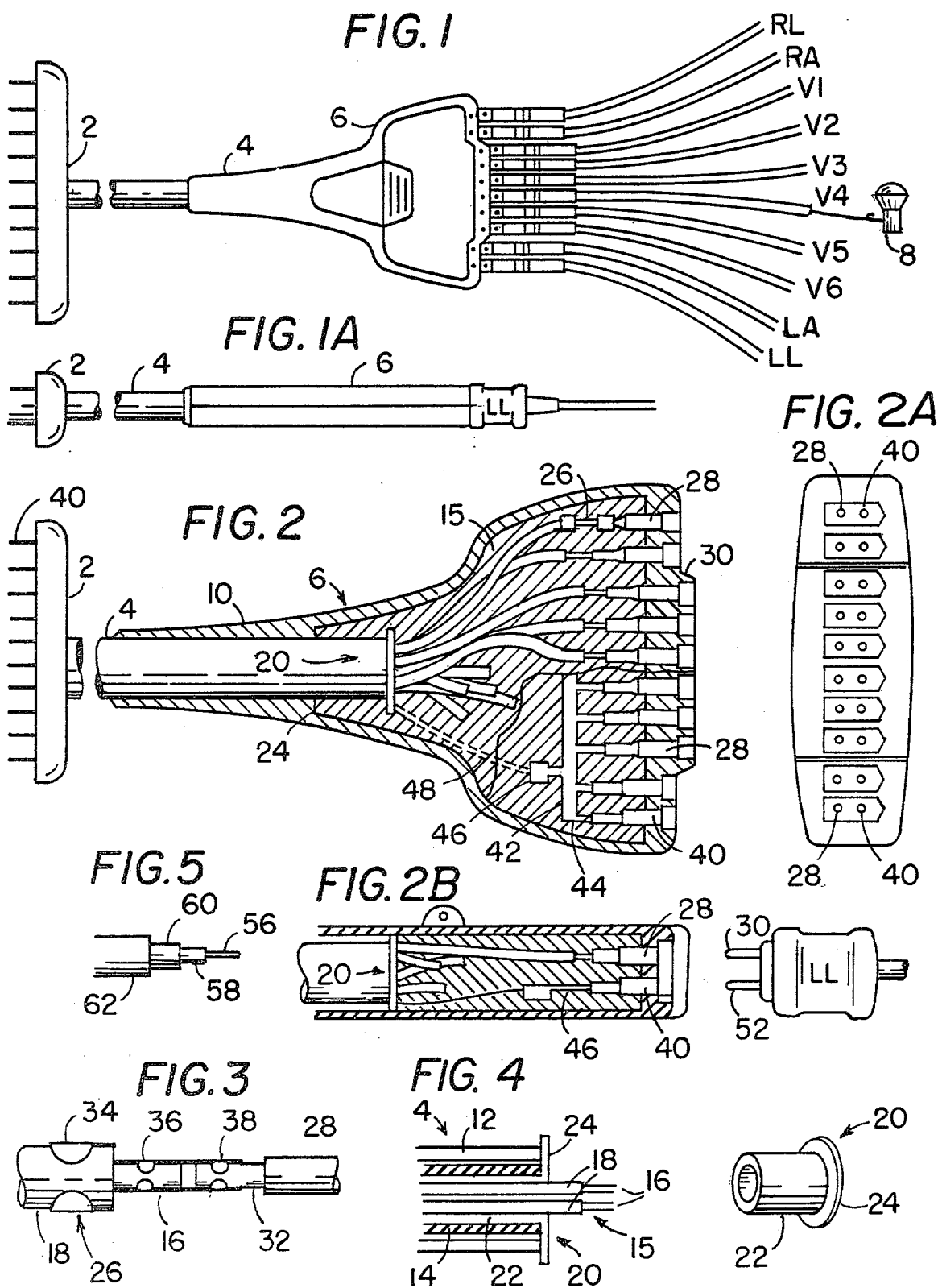

PATIENT CABLE WITH DISTRIBUTED RESISTANCE PROTECTION IN CONDUCTORS

BACKGROUND OF THE INVENTION

EKG machines produce electrocardiograms representing the functioning of a patient's heart from electrical signals supplied by as many as twelve electrodes conductively attached to selected points on the patient's body. If the patient should require resuscitation with a defibrillator while the EKG machine is in operation, some means must be provided for protecting the EKG machine from the high energy electrical pulses that are applied to the patient by the defibrillator. Need for such protection would be unnecessary if the EKG electrodes were removed prior to the application of the defibrillator pulses, but that is not practical because there is often insufficient time. Most EKG machines are equipped with internal circuits that bypass the front end amplifiers in the presence of a defibrillation pulse, but full protection of the machine requires that voltage limiting means be included in each of the leads from the machine to the electrodes attached to the patient's body. Heretofore, this has been accomplished by inserting 6800-ohm, 2-watt carbon composition resistors in series with each lead. The resistors are generally mounted in the yoke at the end of the trunk cable from the machine. In a twelve-lead system, the yoke is heavy and awkward, especially in stress testing where the patient is moving and the yoke must be attached to his body. Furthermore, cables with yokes for this purpose are costly to build.

BRIEF DISCUSSION OF THE INVENTION

Instead of inserting discrete lumped resistors in each lead by mounting them in a yoke as just described, either the leads in a trunk cable leading from the yoke to the EKG machine and/or the individual leads between the yoke and the electrodes that are to be attached to the patient are made of electrically conductive carbon loaded polymer which, by way of example, can be vinyl or polyethylene. The distributed resistance of each polymer lead is sufficient to protect the EKG machine from defibrillation pulses. It has been found that these polymer conductors are rugged, flexible, quite immune to defibrillator pulses and cost very little more than the metallic conductors which they replace.

THE DRAWINGS

FIG. 1 is a top view of a harness of this invention showing an EKG plug, trunk cable, yoke and individual electrode leads, one of which is shown with an electrode attached thereto;

FIG. 1A is an elevation of part of FIG. 1;

FIG. 2 is a top view of a harness of this invention in which certain portions of the yoke are removed in order to permit a view of the internal structure;

FIG. 2A is an end view of the yoke of FIG. 2;

FIG. 2B is an elevation of the yoke of FIG. 2 with certain material removed and includes an elevation of a plug for an electrode lead;

FIG. 3 illustrates one way of physically and electrically connecting a conductor made from carbon loaded polymer to an electrical terminal;

FIG. 4 illustrates one construction of a trunk cable; and

FIG. 5 shows the construction of an electrode lead.

DESCRIPTION OF A PREFERRED EMBODIMENT

In FIG. 1, the harness is illustrated as having a male plug 2 for attachment to an EKG machine and a trunk cable 4 between the plug 2 and a yoke 6. Although not shown in this view, the yoke 6 has female plugs inserted in its end. Corresponding male plugs, respectively attached to electrodes leads RL, RA, V1, V2, V3, V4, V5, V6, LA and LL, are shown as they would be in use. Although each electrode lead is connected to a body electrode, only one electrode 8 is shown.

In FIG. 2, the trunk cable 4 is shown as being retained in the tapered end of a housing 10 of the yoke 6 and projecting into the generally bell-shaped space within the other end.

As can be seen from FIG. 4, the trunk cable 4 has an outer sheath 12 of flexible abrasion-resistant material such as vinyl overlying a shielding sheath 14 made of conductive vinyl. Inside the shielding sheath 14 are the required number of individual leads 15 of this invention, each of which is comprised of a core 16 formed from carbon loaded polymer coated with a suitable flexible insulation 18 such as vinyl. Only two conductors are shown in the interest of clarity. A metal collar, shown separately at 20, is comprised of a hollow cylinder 22 having an outwardly extending flange 24. The cylinder 22 is inserted within the grounding sheath 14 so as to make electrical contact therewith, and the flange 24 closes off the end of the trunk cable 4.

Returning now to FIG. 2, it is seen that the leads 15 are crimped by means 26, illustrated in greater detail in FIG. 3, to the ends of connectors in the form of female sockets 28 that are inserted in the end wall 30 along a line on the upper half of the yoke 6. Any suitable crimping means can be used, but as shown in FIG. 3, the crimping means 26 is comprised of an open channel of metal having tabs extending outwardly on either side. The width of the channel in combination with the length of the tabs is sufficient for them to nearly encircle particular parts of the lead 15 and the shank 32 of a socket 28. The dimensions are such that the tabs 34 extend around the outer coating 18 of a lead 15, the tabs 36 extend around the core 16 of carbon loaded plastic, and the tabs 38 extend around the shank 32 of the female socket 28. Similar crimping connections can be made to the shanks of male sockets 40 contained in the plug 2 at the other end of the leads 15.

As seen in the end view of FIG. 2A and in the cutaway section of FIG. 2, there is a lower row of connectors in the form of female sockets 40. Although not shown in FIG. 2, their shanks are crimped by means such as 26 to tongues 42 that extend from a bus bar 44. A tongue 46 that extends in the opposite direction from the bus bar 44 is crimped by means such as 26 shown in FIG. 3 to a wire 48 that is connected to the flange 24 of the collar 20. After this connection is made, the bell-shaped cavity in the yoke housing 10 is filled with insulating plastic.

FIG. 2B is an elevation of a portion of the yoke 6 showing the female socket connectors 28 and 40 into which the bayonets 50 and 52 of a plug LL are to be inserted. In the enlargement of an electrode lead such as LL shown in FIG. 5, the lead is comprised of a central conductor 56, an insulating layer 58, an electrical shield, 60 and an outer protective sheath 62. The electrical shield 60 of the lead LL is internally connected within the plug LL to the bayonet 52 and the central conductor 46 is connected to the bayonet 50. The manner of such connection is not shown, but is well within the art. Similar connections are made for all the other plugs.

It would be possible to make the central conductor 56 of carbon loaded plastic just as was done in the leads 15 but this is not preferred because the different lengths of the electrode leads would cause different amounts of resistance to be inserted in series with each input to the EKG machine.

What is claimed is:

1. A yoke and trunk cable for coupling the inputs of an EKG machine to the separate leads from electrodes attached to a patient in such manner as to protect the inputs from current resulting from high voltage pulses that appear on the leads when a defibrillator pulse is applied to the patient, comprising a trunk cable comprised of an outer protective sheath containing a conductive shield, a plurality of leads within said conductive shield, each lead having a conductor of an electrically conductive carbon loaded polymer coated with insulating material, the lengths of said leads of carbon loaded polymer being such as to provide an electrical resistance to protect an EKG machine connected to one end of said conductor from a defibrillator pulse applied to the other end, a yoke having a plurality of pairs of connectors, one connector of each pair for receiving a pin connected to a conductor, the other connector of each pair for receiving a pin connected to a shield, means for respectively connecting each of said connectors for receiving a conductor to one of said electrically conductive carbon loaded polymer conductors in said trunk cable, and means for connecting said connectors for receiving a pin connected to a shield to said conductive shield in said trunk cable.

* * * * *